(12) United States Patent
Rudi (10) Patent No.: US 7,262,009 B2
(45) Date of Patent: Aug. 28, 2007

(54) METHOD OF CELL DETECTION

(75) Inventor: Knut Rudi, Vestby (NO)

(73) Assignee: Matforsk; Norwegian Food Research Institute (NO)

(*) Notice: Subject to any disclaimer, the term of this patent is extended or adjusted under 35 U.S.C. 154(b) by 446 days.

(21) Appl. No.: 10/257,493

(22) PCT Filed: Apr. 10, 2001

(86) PCT No.: PCT/GB01/01619

§ 371 (c)(1),
(2), (4) Date: Mar. 18, 2003

(87) PCT Pub. No.: WO01/77379

PCT Pub. Date: Oct. 18, 2001

(65) Prior Publication Data

US 2003/0203374 A1    Oct. 30, 2003

(30) Foreign Application Priority Data

Apr. 10, 2000 (GB) ............................... 0008787.4

(51) Int. Cl.
*C12Q 1/68* (2006.01)
(52) U.S. Cl. .......................................................... 435/6
(58) Field of Classification Search .................... None
See application file for complete search history.

(56) References Cited

U.S. PATENT DOCUMENTS 5,525,471 A * 6/1996 Zeng ............................... 435/6
5,780,278 A * 7/1998 Miller et al. ................ 536/23.7

FOREIGN PATENT DOCUMENTS

| EP | 0517154 A1 | * 12/1992 |
| EP | 0 881 489 | 12/1998 |
| WO | WO98/51693 | 11/1998 |

OTHER PUBLICATIONS

Fang et al., "Transmission of Human T-Cell Leukemia Virus Type 1 to Mice," Journal of Virology, May 1998, vol. 72, No. 5, pp. 3952-3957.*
"Assessment to Cell Viability," Current Protocols in Cytometry, 1997, 9.2.1-9.2.14, Coder, D.M.*
Frankfurt, "Assessment of cell viability by flow cytometric analysis using DNAse exclusion," Experimental Cell Research, Apr. 1983, vol. 144, No. 2, Abstract only.*
Amendment Filed on May 24, 2002 for International Application PCT/GB01/01619.
Amendment Filed on Aug. 22, 2002 for International Application PCT/GB01/01619.
Roth, et al., "Bacterial Viability and Antibiotic Susceptibility Testing with SYTOX Green Nucleic Acid Stain", Applied and Environmental Microbiology, vol. 63, No. 6, Jun. 1997, pp. 2421-2431.
Riedy et al., "Use of a Photolabeling Technique to Identify Nonviable Cells in Fixed Homologous or Heterologous Cell Populations", Cytometry 12:133-139 (1991).
Ormerod et al., "Quantification of Apoptosis and Necrosis by Flow Cytometry", Acta Oncologica, vol. 32, No. 4, pp. 417-424, 1993.
Langsrud et al., "Flow cytometry for rapid assessment of viability after exposure to a quaternary ammonium compound", Journal of Applied Bacteriology 1996, 81, 411-418.
Cimino et al., "Post-PCR sterilization: a method to control carryover contamination for the polymerase chain reaction", Nucleic Acids Research, vol. 19, No. 1, Jan. 1991, pp. 99-107.
O'Brien et al., "Comparison of Cell Viability Probes Compatible With Fixation and Permeabilization for Combined Surface and Intracellular Staining in Flow Cytometry", Cytometry 19:243-255 (1995).
Zhao et al., "Comparison of Cellular Binding and Uptake of Antisense Phosphodiester, Phosphorothioate, and Mixed Phosphorothioate and Methylphosphonate Oligonucleotides", Antisense Research and Development 3:53-66 (1993).
Sheridan et al., "Detection of mRNA by Reverse Transcription-PCR as an Indicator of Viability in *Escherichia coli* Cells", Applied and Environmental Microbiology, vol. 64, No. 4, Apr. 1998, p. 1313-1318.
McKillip et al., "rRNA Stability in Heat-Killed and UV-Irradiated Enterotoxigenic *Staphylococcus aureus* and *Escherichia coli* O157:H7", Applied and Envrionmental Microbiology, vol. 64, No. 11, Nov. 1998, p. 4264-4268.
Norton et al., "Detection of Viable *Listeria monocytogenes* with a 5' Nuclease PCR Assay", Applied Environmental Microbiology, vol. 65, No. 5, May 1999, p. 2122-2127.
Syvanen et al., "A Primer-Guided Nucleotide Incorporation Assay in the Genotyping of Apolipoprotein E", Genomics, vol. 8, pp. 684-692 (1990).
Wahlberg et al., "Rapid detection and sequencing of specific in vitro amplified DNA sequences using solid phase methods", Molecular and Cellular Probes, (1990) vol. 4, pp. 285-297.
McClelland et al., "Effect of site-specific modification on restriction endonucleases and DNA modification methyltransferases", Nucleic Acids Research, 1994, vol. 22, No. 17, pp. 3640-3659.
Pearson et al., "Improved tools for biological sequence comparison", Proceedings of the National Academy of Science of the USA, vol. 85, Apr. 1988, pp. 2444-2448.

(Continued)

*Primary Examiner*—Young J. Kim
(74) *Attorney, Agent, or Firm*—Cantor Colburn LLP (57) ABSTRACT

A method of distinguishing between living and dead cells in a sample, the method includes: (a) contacting the sample with a viability probe which modifies the nucleic acid of dead cells within the sample; and (b) detecting nucleic acid from the cells in the sample, wherein detection involves binding of one or more oligonucleotide probes to a target sequence within the nucleic acid. A method of detecting cells in a sample, the method includes: (a) contacting the sample with a viability probe which labels the nucleic acid of dead cells within the sample; (b) separating the nucleic acid from the cells into labelled and non-labelled fraction; and (c) detecting the nucleic acid in one or both of the fractions.

20 Claims, 4 Drawing Sheets

OTHER PUBLICATIONS

Heid et al., "Real Time Quantitative PCR", Genome Research, vol. 6, 1996, pp. 986-994.

Lebaron et al., "Comparison of Blue Nucleic Acid Dyes for Flow Cytometric Enumeration of Bacteria in Aquatic Systems", Applied and Environmental Microbiology, vol. 64, No. 5, May 1998, pp. 1725-1730.

McKillip et al., "Nucleic Acid Persistence in Heat-Killed *Escherichia coli* O157:H7 from Contaminated Skim Milk", Journal of Food Protection, vol. 62, No. 8, 1999, pp. 839-844.

Marx et al., "Covalent Attachment of Ethidium to DNA Results in Enhanced Topoisomerase II-Mediated DNA Cleavage", Biochemistry, vol. 36, 1997, pp. 15884-15891.

Hardwick et al., "Ethidium Binding Sites on Plasmid DNA Determined by Photoaffinity Labeling", The Journal of Biological Chemistry, vol. 259, 1984, pp. 11090-11097.

L. Herman, "Detection of viable and dead *Listeria monocytogenes* by PCR", Food Microbiology, vol. 14, 1997, pp. 103-110.

\* cited by examiner

METHOD OF CELL DETECTION

FIELD OF THE INVENTION

The present invention relates to methods of assaying cells in a biological sample, in particular to methods which can distinguish between living and dead cells.

DESCRIPTION OF THE RELATED ART

In many circumstances it is desirable to investigate a population of cells within a sample in such a way that qualitative or quantitation information relating to living cells only within that population is obtained or a comparison between the total population of living and dead cells and living cells only can be made. This is particularly the case when monitoring a patient for vital or bacterial infection or the presence of cancerous cells and assessing the efficacy of a treatment regimen therefor or for analysis of an environmental sample that may be contaminated, e.g. a water sample.

Quantification of viable bacterial populations is important in many areas of microbiology, including public health, biotechnology, the food, water and pharmaceutical industries and in environmental studies. As discussed by Sheridan, G. E. C. et al. in Applied and Environmental Microbiology, April 1998 pp. 1313-1318, conventional methods for detecting bacterial pathogens typically involve culturing the organisms in selective media and identifying isolates according to their morphological, biochemical and/or immunological characteristics. These methods take several days to perform and in any event, identification methods based on phenotypic properties are rather unreliable. Moreover, bacteria may be in a state where they are viable and infectious but not culturable and thus not detectable by these traditional methods.

Flow cytometry can be used to perform dead cell discrimination based on the dramatic increase in cell membrane permeability observed on cell death. The techniques may involve physical separation methods or be based on differential light scatter or staining by fluorescent probes. In these cases, discrimination takes place at the whole cell level.

However, methods of detection and identification of cell populations which rely on direct nucleic acid assays, e.g. which involve an oligonucleotide probe, are capable of being very specific and can also be extremely sensitive, when coupled, for example, with PCR. However, as stated by Sheridan et al. supra, a significant disadvantage of DNA-based methods is that they cannot distinguish between living and dead organisms. This is because DNA is rather stable and survives intact although the organism is dead and is therefore able for example to act as a template for PCR. Nucleic acid-based methods which could be applied directly to samples to give an indication of the viability of certain cell populations, e.g. microbes, would be of great significance for many industrial, environmental and medical applications.

Attempts have been made to devise assays which rely on detection of RNA which is generally much less stable than DNA and therefore could be an indicator of the number of live cells in a sample. However the results of these experiments suggest that RNA may not in fact yield accurate information as to whether the cells are alive or dead. The stability of the RNA molecule is sequence dependent and may vary by several orders of magnitude. Furthermore, both the stability and expression levels are affected by environmental conditions (McKillip, J. L. et al., Appl. Environ. Microbiol. [1998] 64 pp 4264-4268 and Norton, D. M. et al., Appl. Environ. Microbiol. [1999] 65 pp 2122-7).

Thus a need remains for a detection method which can utilise the specificity and sensitivity of a nucleic acid based assay while allowing discrimination between live and dead cells within the cell population of interest.

SUMMARY OF THE INVENTION

The inventors have found that certain viability probes can be used which selectively interact with nucleic acid from dead cells and thus allow discrimination between dead and live cells at the nucleic acid level, typically by influencing the generation of a signal in a nucleic-acid based assay. The dead-cell nucleic acid is effectively exposed due to the permeability of the cell membrane in dead cells while the nucleic acid in live cells is protected and remains unmodified by the viability probe.

Thus, according to one aspect of the present invention is provided a method of detecting cells in a sample, said method comprising:

(a) contacting the sample with a viability probe which modifies the nucleic acid of dead cells within the sample; and (b) detecting nucleic acid from the cells in the sample.

Generally, the method of the invention will be performed so that only living cells within the sample are actually detected. The method of the invention allows differentiation between those cells in the sample which are dead and those which are living; therefore, alternatively viewed, the present invention provides a method of distinguishing between living and dead cells in a sample, said method comprising:

(a) contacting the sample with a viability probe which modifies the nucleic acid of dead cells within the sample; and (b) detecting nucleic acid from the cells in the sample.

As discussed in more detail below, the 'modification' will typically be by way of labelling the nucleic acid and/or inactivating it. Not all the nucleic acid within all the dead cells will necessarily be modified during the method. Equally, some of the living cell nucleic acid may be modified. A viability probe may be chosen which is selective for a particular population of cells within the sample. The viability probe may also be selective amongst the nucleic acid within a given cell, for example modifying DNA in preference to RNA. The nucleic acid detection method will typically be designed to target sequences of nucleic acid which would have been significantly modified in dead cells by the particular viability probe used. The nucleic acid may be inactivated in that its ability to generate a signal according to the detection means chosen is prevented or significantly reduced.

Inter alia, the method of the present invention provides a simple method for the separate detection, using a nucleic acid-based assay, of living and dead bacteria. The method can be applied under natural conditions to analyse complex communities.

Alternatively viewed, the invention provides a method of excluding dead cells from an analysis of a cell population within a sample, said method comprising:

(a) contacting the sample containing said cell population with a viability probe which modifies the nucleic acid of the dead cells within said cell population; and (b) detecting nucleic acid from the cell population.

The term 'cell population' refers to the cell types which the method is being performed to detect. This may be all the cells present in the sample, all the prokaryotic cells present in the sample or any other group of cells which it is desired to investigate. The cell population will be any distinguishable class or group of cells which can be identified by the nucleic acid detection method. Thus, a particular detection method will be chosen on the basis of how specific the cell population of interest is. Therefore regions within the nucleic acid which will be targets for the detection method will be common to all the cells within the cell population of interest. The target region may be common to all prokaryotic cells or just a particular strain of microorganism, depending on the specificity of the assay method and the cell types/microorganisms which it is desired to detect.

By "viability probe" is meant any agent which is able to enter dead cells but not living cells. It will be appreciated that a suitable agent need not be 100% selective, i.e. it is possible that small amounts of the agent will be able to enter living cells. Preferably if the amount of the viability probe is present in a typical dead cell, i.e. the average concentration of the agent in a dead cell is assigned a value 100, then the amount present in a typical living cell, i.e. the average concentration in a living cell will be less than 30, preferably less than 20, more preferably less than 10, e.g. less than 5.

Suitable viability probes are well known in the art and documented in the literature. According to the present invention, the viability probe must be able to interact with nucleic acid in the dead dells, by binding, e.g. covalently or through hydrogen bonding, or in any other way. As discussed in more detail below, the viability probe will typically act by inactivating or labelling the dead cell-originating nucleic acid.

Suitable agents may be chemicals such as dyes which associate with nucleic acid or enzymes, for example DNAses or RNases or restriction enzymes. Non-enzymatic viability probes e.g. chemicals are preferred as they are smaller and better able to cross the dead cell membranes, although still unable to breach living cell membranes.

Peptides and oligonucleotides, e.g. antisense sequences or PNA probes are further examples of suitable viability probes. These are generally small and therefore can enter dead cells more easily than enzymes. These molecules may be able to prevent or reduce nucleic acid detection directly, e.g. by inhibiting PCR but more usually they will be used to label the dead cell nucleic acid in a way which can then be utilised to separate dead cell nucleic acid from nucleic acid derived from living cells. Alternatively, a moiety may be bound to the peptide/oligonucleotide which can modify the nucleic acid to inhibit signal generation, e.g. after photo-induced covalent binding. The peptide/oligonucleotide is thus acting as a carrier and may allow for specific binding and modification of a targeted region of nucleic acid. Suitable inhibiting moieties include EMA and 4'-AMDMIP.

Dyes which act as living/dead markers are known in the art and include ethidium bromide monoazide (EMA), 4'-AMDMIP, AMIP, 5-MIP(5-methylisopsoralen) (Cimino, G. D. et. al. Nucleic Acids Research (1991) Vol. 19. No. 1 pp 99-107), SYTO 59 red fluorescent nucleic acid stain and SYTOX green nucleic acid stain, LIVE/DEAD BacLight Bacterial Viability Kit, ViaGram Red+Bacterial Gram Stain and Viability Kit (Molecular Probes). Further agents include BODIPY FL-14-dUTP, fluorescin concanavalin A, propidium iodide, YO-PRO-1 dye, Alexa Fluor 488 annexin V, C4-BODIPV 500/510 CY and Hoechst 33258 (Molecular Probes) which are particularly suitable for use in methods which relate to assays of eukaryotic cells wherein some of the cells have undergone apoptosis.

Many suitable viability probes are fluorescent dyes but it is not the ability to fluoresce which is primarily being utilised in order to distinguish between living and dead cells according to the methods of the present invention. Instead, it is the ability of these agents to associate with and in some way alter the character of the nucleic acid from dead cells which enables differentiation. The viability probe may remain bound to the nucleic acid (i.e. the dead-cell originating nucleic acid is labelled) and this association between the viability probe and the nucleic acid utilised to separate dead cell originating nucleic acid from live cell originating nucleic acid.

This is preferably achieved by providing a binding partner to the viability probe, typically attached to a solid support. For example, an antibody to the viability probe may be provided on a solid support and the nucleic acid from the sample contacted with the solid support to allow specific binding of the viability probe/dead cell nucleic acid complex to the antibody attached to the solid support. The living cell originating nucleic acid with no associated viability probe would not bind and can simply be run off and assayed. This method has the advantage that the nucleic acid which is attached to the solid support via the viability probe and the antibody thereto could be eluted and assayed separately; in this way information regarding the size of the dead cell population within the sample can be generated.

Thus, according to one embodiment of the present invention is-provided a method of detecting cells in a sample, said method comprising:

(a) contacting the sample with a viability probe which labels the nucleic acid of dead cells within the sample;

(b) separating the nucleic acid from the cells into labelled and non-labelled fractions; and (c) detecting the nucleic acid in one or both of the fractions.

The present invention also provides a method of differentiating between living and dead cells in a sample, said method comprising:

(a) contacting the sample with a viability probe which labels the nucleic acid of the dead cells;

(b) separating the nucleic acid from the cells into labelled and non-labelled fractions; and (c) detecting the nucleic acid in one or both of the fractions.

Chemicals such as the dyes discussed above can act in this way, as can oligonucleotides, peptides, polypeptides, proteins and fragments thereof.

However, in a preferred embodiment the viability probe inactivates the dead-cell nucleic acid and thus may conveniently be referred to as an "inactivator". By "inactivates" it is meant that the viability probe prevents or greatly reduces any signal being generated by the nucleic acid during the nucleic acid detection step. This could be achieved by degradation of the dead cell nucleic acid using DNases or RNases or cutting specific regions using restriction enzymes. Chemicals can be used as viability probes to inactivate the nucleic acid, by degradation or by an alternative modification which in some way inhibits the nucleic acid assay, i.e. prevents the dead-cell nucleic acid acting as a template in the detection step. Typical of such an inactivator is EMA which is capable of binding covalently to DNA upon photoactivation and is able to inhibit PCR when covalently bound to or otherwise associated with DNA. 4'-AMDMIDP has also been shown to inhibit PCR by covalent attachment to DNA (Cimino, G. D. et al., supra).

A number of different techniques for detecting nucleic acids are known and described in the literature and any of these may be used according to the present invention. At its simplest the nucleic acid may be detected by hybridisation to a probe and very many such hybridisation protocols have been described (see eg. Sambrook et al., 1989, Molecular Cloning: A Laboratory Manual, 2nd Ed. Cold Spring Harbor Press, Cold Spring Harbor, N.Y.). Most commonly, the detection will involve an in situ hybridisation step, and/or an in vitro amplification step using any of the methods described in the literature for this. Thus, as mentioned, techniques such as LAR, 3SR and the Q-beta-replicase system may be used. However, PCR and its various modifications eg. the use of nested primers, will generally be the method of choice (see eg. Abramson and Myers, 1993, Current Opinion in Biotechnology, 4: 41-47 for a review of nucleic acid amplification technologies).

Other detection methods may be based on a sequencing approach, for example, the minisequencing approach as described by Syvänen and Söderlund, 1990, Genomics, 8: 684-692.

The results of the PCR or other detection step may be detected or visualised by many means, which are described in the art. For example the PCR or other amplification products may be run on an electrophoresis gel eg. an ethidium bromide stained agarose gel using known techniques. Alternatively, the DIANA system may be used, which is a modification of the nested primer technique. In the DIANA (Detection of Immobilised Amplified Nucleic Acids) system (see Wahlberg et al., Mol. Cell Probes 4: 285(1990)), the inner, second pair of primers carry, respectively, means for immobilisation to permit capture of amplified DNA, and a label or means for attachment of a label to permit recognition. This provides the dual advantages of a reduced background signal, and a rapid and easy means for detection of the amplified DNA.

The amplified nucleic acid may also be detected, or the result confirmed, by sequencing, using any of the many different sequencing technologies which are now available, eg. standard sequencing, solid phase sequencing, cyclic sequencing, automatic sequencing and minisequencing.

The step of nucleic acid detection will preferably involve binding of one or more oligonucleotide probes (conveniently referred to herein as a detection probe) to a target nucleic acid sequence. These probes may be primers for a nucleic acid amplification reaction, such as PCR, RT-PCR, NASBA, isothermal amplification, ligase chain-reaction etc. Alternatively, a labelled probe may be used and assayed directly. Preferably, the nucleic acid detection step will involve an amplification reaction. The use of detection probes means that target nucleic acid sequences can be selected which are specific to the cell population of interest, e.g. to a particular species or strain of microorganism.

Clearly, where the nucleic acid has been degraded, e.g. by DNases or RNases or cut in a relevant region by restriction enzymes, the detection probes will be unable to bind to the target nucleic acid sequences and so the dead cell originating nucleic acid is unable to act as a template and generate a signal. All the signal generated, e.g. following amplification and separation by gel electrophoresis, will therefore derive from the nucleic acid of living cells. In this way the information about the living cell population in a sample is generated. Such information, as discussed above, is often more valuable than knowing the size of a population of cells which includes living and dead cells.

Inactivators which modify the nucleic acid in other ways may also prevent signal generation via the viability probes. Binding of the inactivator to the nucleic acid may physically prevent binding of the detection probe or the operation of enzymes involved in the detection method, e.g. a polymerase. Enzymes such as polymerases may be inhibited by the viability probe; it has been shown, for example, that EMA can inhibit PCR even when it is not covalently bound to the nucleic acid. The viability probe may remain associated with the nucleic acid, acting as an inactivator or label (e.g. covalently bound EMA).

Alternatively, the viability probe may modify the nucleic acid to inactivate and/or label it but will not itself remain associated therewith (e.g. enzymes or chemicals which degrade the nucleic acid). Methyltransferases (McClelland, M. et al., Nucleic Acids Research (1998) 22, 17, pp 3640-3659) may label dead cell nucleic acid. The modification caused by the viability probe will preferably be non-reversible, e.g. as a result of covalent bonding to the dead cell nucleic acid or degradation thereof. Viability probes which themselves label the nucleic acid will preferably associate strongly with the nucleic acid. Modifications caused by viability probes which do not themselves remain associated with the nucleic acid will preferably be essentially non-reversible, at least under the conditions of the detection method.

The viability probe will preferably bind to the nucleic acid, this binding may be temporary, as in the case of a DNase. Binding includes covalent binding as well as by hydrogen bonding or any other form of association.

Typically, after contacting the sample with a viability probe which is able to selectively enter dead cells and thus modify the nucleic acid therein, the cells are lysed and the nucleic acid from the whole sample isolated for performance of the detection method. Thus, in a preferred embodiment, the nucleic acid from all the cells in the sample is mixed prior to the nucleic acid detection method. Information about just the live cell population or in certain circumstances just the dead cell population can be obtained because of the physical difference between live and dead cell nucleic acid which has been caused by the viability probe. As discussed above, where the viability probe is a DNase or RNase, the 'difference' will be that the dead cell nucleic acid does not exist as such, as it has been degraded. Typically, the viability probe enzyme e.g. DNase, is denatured on cell lysis and so is not available to degrade the nucleic acid from living cells.

The present methods can therefore be contrasted with those of differentiation by flow cytometry, which rely on a discrimination at the cellular level which generally depends on a visual assessment of whether the whole cell is dead or living. Thus there will be a sorting or physical separation of the living and dead cells during flow cytometry. The fact that the sample can be contacted with a viability probe and then a nucleic acid detection step performed on the sample without ever having to differentiate living from dead cells makes the method of the present invention very convenient. In addition, the method can be fully automated and does not require any judgement to be made, such as when gating cells during flow cytometry, as to whether any given cell is living or dead. Also, only liquid samples with low particle amounts can be processed by flow cytometry.

As mentioned above, a nucleic acid detection method which involves an amplification step is preferred. Amplification primers are added to the sample and the well known cycles of the selected amplification protocol performed. The dead cell originating nucleic acid may have been enzymatically degraded and thus only the live-cell originating nucleic acid can be amplified. Alternatively the dead-cell nucleic acid may have been chemically modified so that the amplification reaction is inhibited, possibly by preventing primer binding or enzyme function. In any event, the amplification product will be derived solely or essentially from the living-cell nucleic acid and can be analysed by conventional techniques to obtain an estimate of the amount of target nucleic acid in the original sample and thus of the number of living cells within a given cell population in the sample. Conveniently, the amplification products will be stained, e.g. using ethidium bromide and then separated, e.g. on an agarose gel.

The methods of the invention may conveniently be performed utilising the protocol described in WO98/51693. Thus, the cells in the sample are captured by binding to a solid support, the cells are contacted with the viability probe and then the cells are lysed. The released nucleic acid is then bound to the same solid support before being analysed. As discussed in WO98/51693, the contents of which are incorporated herein by reference, the bound nucleic acid may be analysed while still bound to the solid support or eluted from the solid support for performance of the detection method. The solid support will preferably comprise a particulate material, preferably magnetic beads. Cells and nucleic acid are conveniently bound to the sold support by precipitation.

In a particularly preferred embodiment, bacteria from e.g. a food sample, are captured on a solid support, the bacteria are then contacted with the viability probe e.g. EMA and then exposed to light. DNA is then purified and analysed. The use of a magnetic or magnetisable solid support enables convenient manipulation of the cells/nucleic acid during the method.

The term "cell" is used herein to include all prokaryotic (including archaebacteria) and eukaryotic cells and other viable entities such as viruses and mycoplasms. All cells must show a significant increase in the ability of certain agents to cross the outer membrane, capsid etc. on cell death. Representative "cells" thus include all types of mammalian and non-mammalian cells, plant cells (provided the selected viability probe is able to cross the cellulose cell wall), algae, fungi, protoplasts, bacteria, bacteriophages, mycoplasms, protozoa and viruses.

The sample may thus be any material containing nucleic acid within such cells, including for example foods and allied products, clinical and environmental samples. Thus, the sample may be a biological sample which may contain viral or other cellular material as discussed above. Representative samples thus include whole blood and blood-derived products such as plasma or buffy coats, urine, faces, cerebrospinal fluid or any other body fluids, tissues, cell cultures, cell suspensions etc., and particularly environmental samples such as soil, water or food samples.

The sample may also include selectively pure or partially purified starting material, such as semipure preparations obtained by a cell separation process.

The difference between a living cell and a dead cell is not easy to define in general terms for all cells but for the purposes of the present invention, distinction relies on the fact that a dead cell exhibits greatly enhanced permeability to viability probes. Generally, live cells will be culturable, i.e. can multiply to form colonies on agar plates or produce visible turbidity in broth. Such a definition may not be appropriate in all circumstances, e.g. in the case of viruses which require host cells to replicate. Nevertheless, for a given target cell of interest, parameters can readily be established as indicative of a living cell, crucial to the determination will be the ability of a viability probe to enter the cell. In the case of bacteria, it should be noted that bacteria in a viable but non-culturable state (i.e. which can be 'resuscitated' to the normal culturable state under certain conditions) are considered to be living and their membranes do not have enhanced permeability.

The nucleic acid which is modified by the viability probe may be DNA, RNA or any naturally occurring or synthetic modification thereof, and combinations thereof. Preferably however the nucleic acid will be DNA, which may be single or double stranded or in any other form, e.g. linear or circular.

The viability probe may modify the nucleic acid in an indiscriminate manner, e.g. following binding by or in a discriminate manner targeted to a particular region of the nucleic acid e.g. by use of a restriction endonuclease. Generally there will be no discrimination, other than between living and dead cells, at the viability probe level. The viability probe will typically be able to enter different types of dead cells of which the cell population of interest is only a proportion. Alternatively, viability probes may be selected which are able to enter the dead cells of interest more easily than other dead cells i.e. the viability probe is able to target the cells of interest. This enables a lower overall concentration of viability probe to be used and may enhance the selectivity of the method.

The nucleic acid detection can introduce a level of specificity which can distinguish between different populations of living cells. For example, a probe can be used which binds to a target region of nucleic acid which is particular to a certain microorganism which it is desired to assay. Likewise eukaryotic cells of interest can be assayed by selection of a probe which hybridises to a target region of nucleic acid which is specific to a certain cell type, for example to a particular cancer cell. As discussed above, such probes may be labelled or conveniently be used in an amplification reaction.

A further advantage of the methods of the present invention is the ability of the viability probe to modify free nucleic acid present in the sample, i.e. nucleic acid which is not contained within cells—either living or dead. The modification may be by any of the methods described above, including enzymatic degradation, chemical modification to inhibit the nucleic acid acting as a template in a detection method and labelling to allow segregation of nucleic acid from living cells from other nucleic acid in the sample. Thus free nucleic acid in the sample can be excluded from the assay. The methods can accurately determine the population of living cells within the sample and not over-exaggerate the living cell population because of signal generated by dead cells or free nucleic acid. Thus in a preferred embodiment of the present invention, the viability probe modifies the nucleic acid of dead cells and free nucleic acid within the sample.

The method of the present invention is suitable for analysing cell death itself, particularly by necrosis and apoptosis. Necrosis typically being induced by extracellular conditions and resulting in an early membrane permeabilization; apoptosis being associated with programmed cell death and exhibiting a rather delayed permeability in the cell membrane (O'Brien, M. and Bolton, W., Cytometry (1995) 19, pp 243-255). The number of dead cells can be analysed by comparing the results of a method of the present invention as compared to a method which does not distinguish between living and dead cells and uses no viability probe. Alternatively, when the present invention is performed in such a way that the modification caused by the viability probe is used to separate the dead cell population from the living cell population, then qualitative and quantitative information about the dead cell population can be obtained directly.

The various reactants and components required to perform the methods of the invention may conveniently be supplied in kit form. Such kits represent a further aspect of the invention.

At its simplest, this aspect of the invention provides a kit for detecting cells in a sample comprising:
(a) a viability probe;
(b) means for performing nucleic acid detection.

The invention thus also provides a kit for distinguishing between living and dead cells in a sample comprising:
(a) a viability probe;
(b) means for performing nucleic acid detection.

Means (a) and (b) will be as described and discussed above, in relation to the methods of the invention. (b) will typically comprise one or more detection probes as defined herein. The kit will optionally contain (c), means for lysing the cells. In those methods wherein the living and dead cell nucleic acid fractions are separated prior to nucleic acid detection, the kit may optionally contain (d), a binding partner to the viability probe which is preferably bound to a solid support.

BRIEF DESCRIPTION OF THE DRAWINGS

The invention will now be described in more detail in the following non-limiting Examples with reference to the drawings in which.

Panel A: The ethidium bromide stained (10 µg/ml) amplification products were separated on a 1% agarose gel for 45 minutes at 100 volts. neg=sample without DNA; mw=lambda BsteII cut molecular weight marker.

Panel B: The signal intensities were determined as pixel values in an 8 bit grayscale by using the program Gel-Pro ANALYZER software (Medica Cybernetics, Silver Spring. Md.). The relative signal intensities for the EMA treated samples are given as a percentage of the untreated samples.

DETAILED DESCRIPTION

EXAMPLE 1

PCR Inhibitor Effect of EMA Covalently Bound to DNA Through Photoactivation

The PCR inhibitory effects of both photoactivated, and unactivated EMA were investigated for pure DNA. PCR amplifications were carried out on dilution series of 1000, 100 and 10 µg/ml EMA. The 16S rDNA gene was amplified through the application of the forward primer 5'TGGCTCA-GATTGAACGCTGGCGGC3' and the reverse primer 5'CTTGTTACGACTTCACCCCA3'. These primer sites are universally conserved for eubacterial 16S rDNA.

The PCR amplifications were done using the GeneAmp 9700 PCR amplification system (PE biosystems, Norwalk, Conn., USA). The 50 µl PCR reactions contained 10 pmol of each primer, 200 µM dNTP, 10 mM Tris-HCl (pH 8.8), 1.5 mM $MgCl_2$, 50 mM KCl, 0.1% Triton® x-100, 1 U DynaZyme™ Thermostable DNA Polymerase (Finnzymes OY, Espoo, Finland) and 2 ng template. The cycling parameters were: 94° C. for 30 s, 55° C. for 30 s and 72° C. for 1 minute.

The cycling step was repeated 25 times. The samples were heated to 94° C. for 5 minutes prior to the amplification, and an extension step at 72° C. for 7 minutes was included after completion of the amplification reactions.

Figure 1:
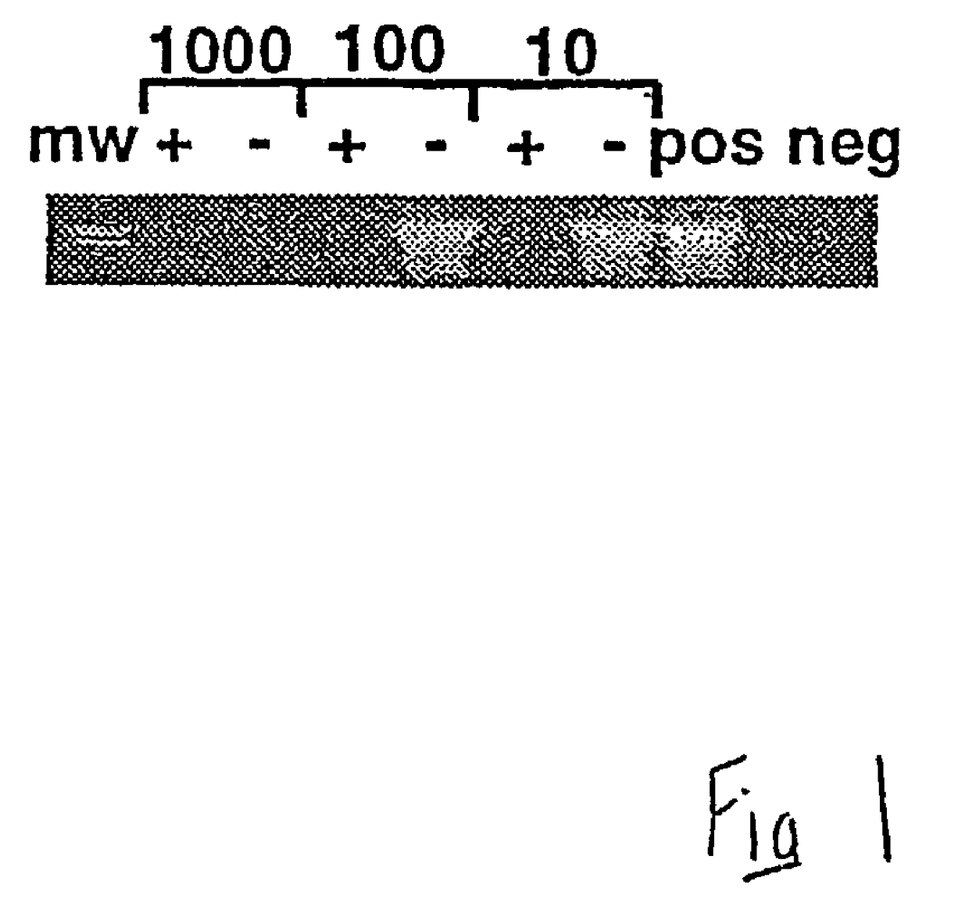
FIG. 1 shows the results on EtBr-stained agarose gel electrophoresis of the separation of PCR amplification products of DNA which had been contacted with EMA. pos=sample without EMA; neg=sample without DNA; mw=lambda BsteII cut molecular weight marker.

For each dilution series PCR was employed both on samples where EMA had been covalently photoactivated to DNA through illumination with a Luxor 18W type FL-185 lamp (Luxor ASA, Oslo, Norway) at 5 cm for 15 minutes, and on samples where EMA had been added to the DNA in the dark. For the highest concentration (1000 µg ml), both the photoactivated and non activated EMA inhibited the PCR reaction. For 100 and 10 µg/ml, the photoactivated EMA inhibited PCR, while PCR for the unactivated EMA was not inhibited (FIG. 1). 10 µg/ml amplification products were separated on a 1% agarose gel for 45 minutes at 100 volts. The conclusion from these experiments is that EMA covalently bound to DNA is sufficient to inhibit PCR amplification, and that EMA by itself is only inhibitory to PCR at high concentrations.

EXAMPLE 2

Application of EMA for Selective PCR Amplification of DNA from Living *E. coli*

*E. coli* was killed by ethanol, heat, and formaldehyde to test the effect of EMA as a living/dead stain. In these experiments aliquots of approximately $10^8$ cells of *E. coli* were pelleted in a microcentrifuge at 8000 rpm for 5 minutes, the supernant removed, and the cells resuspended in 50 µl of the respective liquids; water 96% ethanol, and 2% formaldehyde. The ethanol and formaldehyde treated samples were incubated at room temperature, while the water samples were incubated both at room temperature and at 95° C. All samples were incubated at the respective temperatures for 5 minutes.

The bacteria were subsequently pelleted by centrifugation, the supernatant removed, and the cells resuspended in 50 µl water. EMA was added at a concentration of 10 µg/ml to the test samples, while for the controls, no EMA was added.

All the samples were exposed to light for 10 minutes. Subsequently, the samples were resuspended in 500 µl 4 guanidine thiocyanate (GTC) and 1% sarkosyl containing 1U Dynabeads DNA DIRECT beads (Dynal AS, Oslo, Norway). Incubation was continued at room temperature for an additional 5 minutes. 1 ml 96% ethanol was added, and after 5 minutes the samples were washed twice with 1 ml 70% ethanol. The bead and DNA complex was then resuspended in 50 µl water, and finally heated to 65° C. for 10 minutes to remove residual ethanol. 2% of the purified DNA was used in each amplification reaction as described above.

Figure 2:
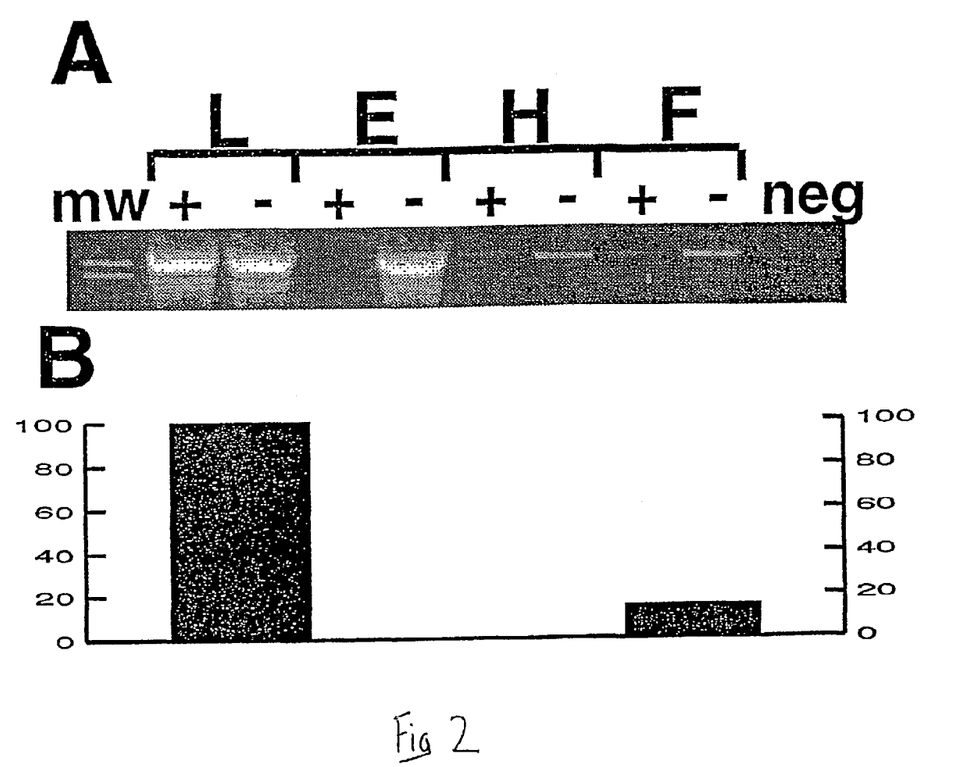
FIG. 2 shows the results of-EtBr-stained agarose gel electrophoresis of the separation of PCR amplification products of DNA from living bacteria treated with EMA (A), and signal intensities for the EMA treated samples relative to the untreated samples (B) (L)=unexposed and living; (E)=ethanol; (H)=heat and (F)=formamide treatment. (+) EMA added; (−)=no EMA added.

There were significant differences in the PCR signal intensities between the controls and the EMA sample for all the killing means, while there were no differences for the living bacteria (FIG. 2). The difference in signal intensities between the treated sample and the control were about 100% both for the bacteria killed with ethanol and the bacteria killed by heat, while the difference was 85% for the formaldehyde treated sample. The differences in effects may possibly be related to how the killing agents permeabilize the cell membranes. Alcohols and heat act by destroying cell membranes, while formaldehyde is an alcylating agent with no profound effect on cell membranes. There did not seem to be a difference in the effect of EMA related to whether the DNA is single or double stranded. The PCR inhibition was 100% both for the ethanol (double-stranded DNA), and the heat (single-stranded DNA) killed bacteria. Increasing the amount of EMA to 100 μg/ml did not result in a better discrimination between the viable and dead bacteria. However, this EMA concentration reduced the amplification efficiency for the living bacteria.

Comparison of signal intensities for the controls indicated that the yield of the DNA purification and/or amplification efficiency is affected by the treatment schemes. Both the heat-treated, and formaldehyde treated samples gave a lower yield as compared to the untreated samples and the samples treated with 96% ethanol.

EXAMPLE 3

Effect of DNase on Heat-treated *Campylobacter jejuni* Type Strain DSMZ 4688$^T$ (Deutsche Samlong von Mikroorganismen und Zellkulturn GmbH, Braunshweig, Germany

*Campylobacter jejuni* is recognised as a leading human food-borne pathogen. The traditional diagnostic testing for *C. jejuni* is not reliable due to special growth requirements, and the possibility that this bacterial can enter a viable but non culturable state (VNC). The following experiment describes a 5'-nuclease PCR assay for quantitative detection of *C. jejuni*, wherein external DNases are added to reduce the PCR signal from free DNA and the exposed DNA of dead bacteria.

The *C. jejuni* strain was plated on blood agar; 1.5 ml from 48 hr culture was pelleted at 6000×g for 7 min at 4° C., washed and resuspended in water, and transferred to microcentrifuge tubes.

The effect on the DNA stability at room temperature after heat-treatment of the cultures, and after addition of DNase was investigated. $1.7\pm0.8\times10^7$ cells (with DNase) and $5.0\pm0.6\times10^7$ cells (without DNase) of *C. jejuni* type strain were used in these experiments. The cultures were incubated at 20, 55, 72 and 100° C. for 5 min, and 121° C. for 5 min. One set of tubes were then incubated further at room temperature, and samples for PCR analysis removed at intervals of 5, 15, and 30 min, 1 h, 6 and 24 hrs, and 5 days. 10 U RQl DNase (Promega, Madison, Wis., USA) and 1× DNase buffer were added to another set of tubes before the incubation at room temperature. Aliquots were analyzed after 5, 15 and 30 min, and after 1 hr, 6 and 24 hours. For the PCR analysis, DNA was purified from 10 μl aliquots from the respective time-points, and the subsequent 5'-nuclease PCR assay performed as described below.

DNA Isolation

Dynabeads® DNA Direct I (Dynal AS, Oslo, Norway), 200 μl, were then added to the suspension of bacteria, and the bacteria-bead suspension was incubated at 65° C. for 20 minutes, followed by incubation at room temperature for another 2 minutes. DNA bound to magnetic beads was then drawn to the wall of the microcentrifuge tube by a magnet (MPC®-E, Dynal AS, Oslo, Norway) for 2 minutes. The supernatant containing salts, detergent and cell debris was carefully removed without disrupting the Dynabeads/DNA complex. The beads were washed twice with a washing buffer (buffer 2 from the kit). Finally, the DNA was removed from the beads by resuspending in 40 μl 10 mM Tris HCl, pH 8.0 (buffer 3 from the kit), and incubation at 65° C. for 5 minutes. The beads, now released from the DNA, were collected with the magnet, and the DNA-containing supernatant was transferred to a fresh tube and used directly in the PCR.

TaqMan Probe and Primer Design

The probe regions were localized in the completed *C. jejuni* strain NCTC 11168 genome sequence (http://www.sanger.ac.uk/Projects/C. *jejuni*.). The Primer Express™ (version 1.0), ABI Prism™ (PE Biosystems, Foster City, Calif., USA) was used for the primer-probe design, together with guidelines from PE Biosystems. The GCG version of FastA was used to search for sequence similarities to other known sequences.

PCR Fragment Specificity

Specific PCR primers and probe were designed for *C. Jejuni*. The probe region was chosen to optimize specificity and amplification efficiency. First, putative probes were constructed using the primer express program, and then these probes were subjected to a FastA search (Pearson, W. R. and D. J. Lipman, 1991, Improved tools for biological sequence comparison, Proc. Natl. Acad. Sci. USA 85: 2444-2448) in the EMBL database (release 60). An 86 bp fragment located in position 381121 to 381205 relative to the published *C. jejuni* strain NCTC 11168 genome sequence (http://www.sanger.ac.uk.Projects/C. *Jejuni*/) was identified in these screenings. There were no known sequences in the EMBL database with significant homology to this probe region. The most closely related sequence had 57.7% identity, and was located in the putative gene YonO in the complete sequence of *Bacillus subtilis* strain 168. PCR primers were constructed from the positions 381121-381144 (forward), and 381205-381185 (reverse), while the probe is located in the position 381146-381181 (Table 1).

After the probe region was identified on a theoretical basis, the specificity of the selected primers and probes were subjected to a empirical screening. A total of 32 *C. jejuni* isolates, including the type strain, were tested and found specific to the chosen primers and probe. The specificity of the primers and probe were controlled against 13 Campylobacter strains of 11 other species, and a set of 41 species belonging to other genera of phylogenetically related or common foodborne organisms and pathogens, all of which were found negative. In these experiments, the quality of the purified DNA was verified through amplification with universal 165 rDNA PCR primers. In addition, a qualitative PCR with the amplification primers alone was done for selected strains. These experiments confirmed that the amplification primers are specific for *C jejuni*. Unspecific PCR products were not detected. No false negatives were recorded among the 32 isolates tested and no false positives were recorded among the other Campylobacter species, or strains belonging to other genera. This demonstrates the high specificity of the designed primer-probe set. Furthermore, the amplification primers alone were also specific for *C. Jejuni* avoiding potential artefacts in mixed population due to competition for the amplification primers through amplification of targets from other bacteria.

5'-Nuclease-based PCR Assay

Amplification reactions (50 µl) contained a DNA sample (1 µl), 1× TaqMan™ Buffer A, 5 mM $MgCl_2$, 200 µM dATP, dCTP, dGTP, and 400 µM dUTF, 0.02 µM. *C. Jejuni* specific probe, 0.3 µM *C. jejuni* specific primers—see Table 1 below (each), 1 U AmpErase™ Uracil N-glycosylase (UNG), and 2.5 U AmpliTaq Gold™ DNA polymerase.

TABLE 1

Primers and fluorogenic probe

| Probe or primer Sequence (5'-3') | Denaturation temp (° C.)* |
|---|---|
| Primers | |
| Fwd CTG AAT TTG ATA CCT TAA GTG CAG C | 60.4 |
| Rev AGG CAC GCC TAA ACC TAT AGC T | 60.3 |
| Probe | |
| TCT CCT TGC TCA TCT TTA GGA TAA ATT CTT TCA CA | 66.6 |

*Calculated by nearest-neighbor algorithm by the Primer Express ™ program (primer concentrations 300 nM, probe concentration 20 nM, salt concentration 55 nM).

PCR samples and controls were prepared in triplicate. Reaction tubes were MicroAmp® Optical tubes and tube caps were MicroAmp® Optical caps. All consumables were supplied by PE Biosystems, Foster City, Calif., USA.

Before amplification, the PCR mixture was heated to 50° C. in 5 min to let the UNG destroy possibly contaminating PCR products, and 95° C. for 10 min to denature the template DNA. Amplification, profile: 40 cycles of 95° C. for 20 seconds and 60° C. for one minute. Reactions were performed in the ABI Prism® 7700 Sequence Detection System (PE Biosystems, Foster City, Calif., USA). Reaction conditions were programmed and data were analyzed on a power Macintosh 4400/20 (Apple Computer, Santa Clara, Calif., USA) linked directly to the ABE prism® 7700 Sequence Detection system using the SDS 1.6.3 application software (PE Biosystems, Foster City, Calif., USA) as described by the manufacturer.

PCR products were detected directly by monitoring the increase in fluorescence from the dye-labelled *C. jejuni* specific DNA probe. The TaqMan probe consisted of an oligonucleotide with a 5'-reporter dye and a 3'-quencher dye. The reporter dye, FAM (carboxyfluorescein) was covalently linked to the 5' end of the oligonucleotide. The fluorescence of the reporter was quenched by TAMRA (6-carboxy-N,N,N',N'-tetramethylrhodamine), located at the 3' end. When the probe was intact, the proximity of the reporter dye to the quencher dye resulted in suppression of the reporter fluorescence. If the probe was cleaved, the reporter and quencher dyes were separated, causing the reporter dye fluorescence to increase.

The amplification was plotted as $\Delta R_n$, which was the normalized reporter signal (reporter signal minus background), against number of cycles. A threshold signal was chosen, which intersected the amplification curves in the linear region of the semi-log plot. This gave threshold cycles ($C_T$), which is defined as the PCR cycle where an increase in fluorescence first occurred, for each amplification plot. Different amplifications could then be compared by their respective threshold cycles. The $C_T$-values were plotted against log input DNA/cells and gave standard curves for quantification of unknown samples and possibilities to estimate the amplification efficiency in the reaction (Heid, C. A., J. Stevens, K. J. Livak and P. M. Williams, 1996, Real time quantitative PCR, Genome Research 6: 986-994; PE Biosystems, 1997, User bulletin 2; ABI PRISM 7700 Sequence Detection System).

The PCR product was verified with ethidium bromide-stained 2% agarose gels (SeaPlaque® GTG®, Agarose, FMC BioProducts, Rockland, Me., USA). Agarose gel electrophoresis was performed essentially as described by Sambrook et al. (1989) in Molecular cloning: a laboratory manual 2nd ed. Cold Spring Harbour Laboratory Press.

Effect of Externally Added DNases on the Stability of DNA in Heat-Treated Cells

Figure 3:
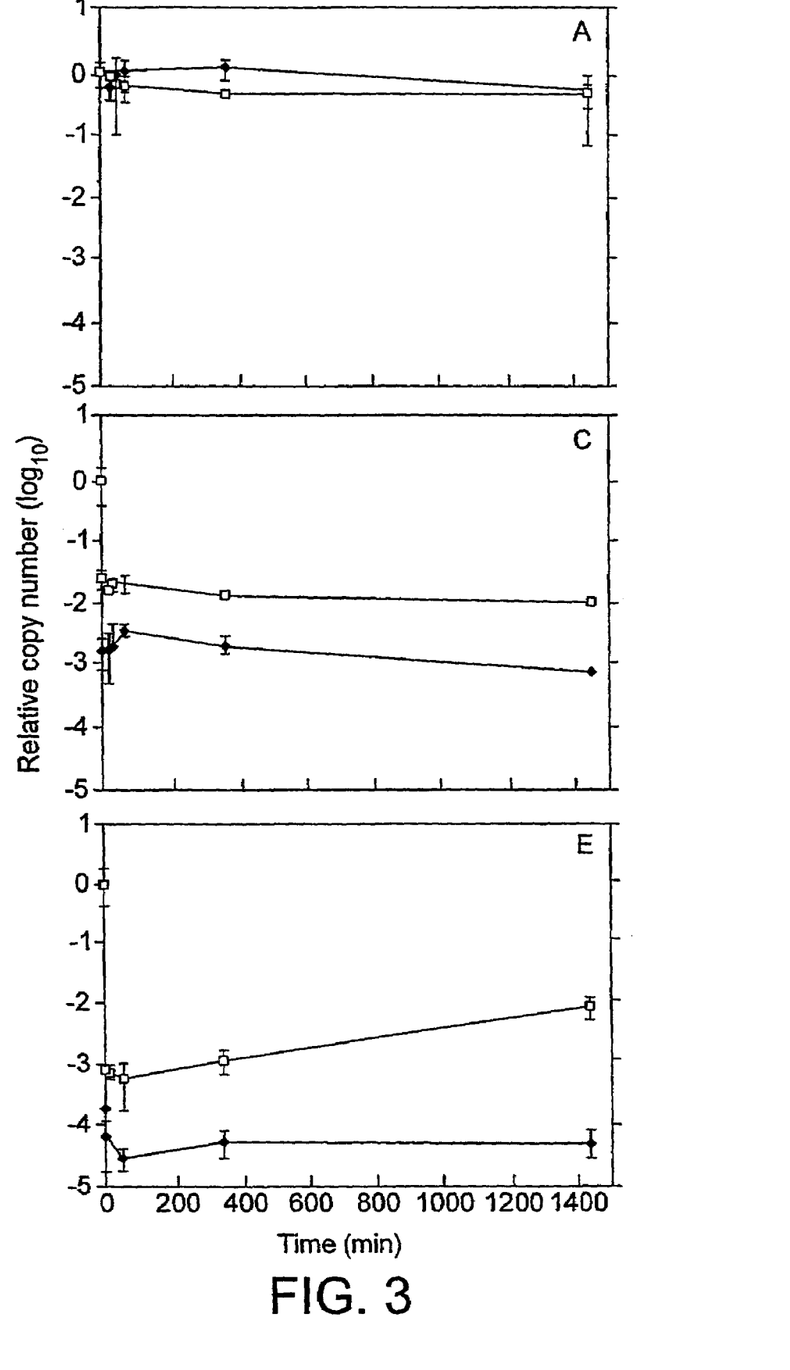
FIG. 3 provides graphical representation of the effect of externally added DNase on the stability of DNA in heat-treated cells. Cells were incubated at (A) 20° C., (B) 55° C., (C) 72° C., (D) 100° C., (E) 121° C., for 5 min (A-D) or 15 min (E) before DNase was added. DNA was quantified by 5'-nuclease PCR after 5, 15 and 30 min, 1, 6 and 24 hrs in both DNase-treated and negative controls. The stability of purified DNA treated with DNase was investigated (F). The amount of DNA with (♦), and without (□) DNase treatment, are given relative to the amount before the heat-treatment. The error bars are standard deviations.

The effect of externally added DNases was compared to control samples in which no DNase was added in cultures incubated at 20, 50, 72 and 100° C. for 5 min, and 121° C. for 15 min. Time series for incubation at room temperature (20° C.) after the heat treatment are shown in FIG. 3.

There was little difference between the DNase treated samples and the control at 20° C. and 55° C. (FIG. 3A and B). For the samples incubated at 55° C. the signal stabilized relatively rapidly at 1 to 3% of the input signal (FIG. 3B). For 72, 100 and 121° C. the addition of DNase resulted in a nearly instant 1 log reduction of the signal compared to control without DNase. No further reductions in the signals were observed neither for the controls, nor the DNase treated samples until 24 hours after the heat treatment (FIGS. 3C, D and E).

The effect of DNase treatment was also investigated on purified DNA from *C. jejuni*. This DNA was very rapidly degraded, and after 30 minutes only about 0.01% of the input material was left. This fraction, however, seemed stable for at least 24 hours after the treatment (FIG. 3F).

The ability of DNase to selectively degrade free DNA and DNA in heat-killed Campylobacter to further reduce the signal generated from the dead cells were investigated. There were no significant differences between the DNase treated, and the untreated samples at 20 or 55° C. The 20° C. experiments show that DNA within intact cells are not degraded by externally added DNases, and did not result in a signal reduction. Although no viable cells could be recovered after the 55° C. treatment, this temperature did not seem sufficient to expose the DNA to externally added DNases. For the samples heated to 72, 100 and 121° C. the addition of DNases nearly instantly reduced the amount of template by 1 log compared to the, untreated samples. For these temperatures the major fraction of DNA in the killed cells was not detected by the assay. In conclusion, applying DNase treatment to reduce the noise signal generated from dead bacteria seems promising for samples that have been treated at temperatures above 72° C. are further examples of suitable viability probes for 5 min or more. This could be of particular utility when organisms have been killed by pasteurization and it is desired to analyse a population introduced after pasteurization. Other temperatures tested simulate alternative methods of treating food to kill microorganisms, such as boiling, 100° C. and canning, 121° C.

EXAMPLE 4

A further series of experiments has been performed using real time quantitative PCR (TaqMan PCR).

TaqMan-based PCR Assay

Amplification reactions (50 µl) contained a DNA sample (1-5 µl), 1× TaqMan™ Buffer A, mM $MgCl_2$, 200 µM dATP, dCTP, dGTP, and 400 µM dUTP, 0.1 µM *E. coli* specific probe, 0.3 µM *E. coli* specific primers (each), and 2.5 U AmpliTaq GoldT™ DNA polymerase. PCR samples and controls were prepared in triplicates. Reaction tubes were MicroAmp® Optical tubes and tube caps were MicroAmp® Optical caps. All consumables were supplied by PE Biosystems, Foster City, Calif., USA. Before amplification, the PCR mixture was heated to 95° C. for 10 mins to denature the template DNA. Amplification profile: 40 cycles of 95° C. for 20 seconds and 60° C. for one minute. Reactions were performed in the ABI prism® 7700 Sequence Detection System (PE Biosysrems, Foster City, Calif., USA).

The amplification was plotted as $\Delta R_n$, which was the normalized reporter signal (reporter signal minus background), against number of cycles. One then chose a threshold signal, which intersected the amplification curves in the linear region of the semi-log plot. This gave threshold cycles ($C_T$), which is detined as the PCR cycle where an increase in fluorescence first occurred, for each amplification plot. Different amplification could then be compared by their respective threshold cycles.

The light activation was done on ice with a OSRAM SLG1000 lamp (OSRAM, Norway) with a 650 W halogen light bulb at a distance of 10 cm.

Results

Time Series for Covalent Binding of EMA to DNA

EMA in concentrations 2 ng/µl, 20 ng/µl and 100 ng/µl were added to purified DNA, and exposed to light for 5 s, 15 s, 45 s, 1 min and 3 min. The amount of DNA that could serve as a template was then tested by real time quantitative PCR. The binding reaction was complete at about 30 s, with a difference in the PCR cycles ($\Delta CT$) until a detectable sigital was obtained at approximately 12 for all concentrations tested—indicating that a fraction of $1/2^{12}=0,000244$ could serve as a PCR template after covalent binding of EMA to DNA.

Time to Light Inactivation of EMA

The EMA was exposed to light for 5 s, 15 s, 30 s, 45 s 1 min, 3 min and 5 min prior to binding to DNA (light activation for 1 min). The EMA concentrations 2 ng/µl, 20 ng/µl and 100 ng/µl were tested. There was no significant difference between the control and the test sample for EMA exposed to light for 30 s or more prior to binding to DNA. This indicates that the ability of EMA to inhibit PCR is rapidly destroyed by light exposure.

This is a very useful property which means that exposure of the reaction to light after a period sufficient to allow the EMA to enter the dead cells and bind to the nucleic acid can effectively 'freeze' the system at that point. This obviates any possible problems with free EMA distorting the results.

Viable/dead Studies on *E. coil* 0157 Strain 765 [Matforsk, AS, Norway]

The strain was killed with 70% isopropyl ethanol for. 30 min. 10 ng/µl and 100 ng/µl EMA were added both to the viable control, and to the killed bacteria. The bacteria were exposed to EMA for 30, 1 min, 5 min, 10 min and 15 min. Exposure to 100 ng/µl for 5 min give the best discrimination with approximately 1 cycle difference for the viable bacteria, and 10 cycles ($1/2^{10}$) for the killed bacteria. Results indicated that for untreated, i.e. viable bacteria, $C_T$ was at 20 PCR cycles for bacteria not exposed to EMA and 21 cycles for bacteria exposed to EMA. For treated, i.e. dead bacteria, $C_T$ was at 20 PCR cycles for bacteria not exposed to EMA but at 30 for bacteria exposed to EMA. Microscopic examination of the staining of the viable population indicated that there was a fraction of dead bacteria, which can explain the slight difference between the control and the EMA treated bacteria.

---

The invention claimed is:

1. A method of excluding dead cells from an analysis of a cell population within a sample, said method comprising:
   (a) contacting the sample with a viability probe which modifies the nucleic acid of dead cells within the sample,
   wherein said viability probe selectively interacts with nucleic acid from dead cells, such that said nucleic acid in living cells remains unmodified by the viability probe;
   (b) lysing the cells after step (a) and after cell lysis allowing the nucleic acid from both living and dead cells to mix prior to performance of step (c); and
   (c) detecting nucleic acid from the living cells in the sample, wherein detection involves binding of one or more oligonucleotide probes to a target sequence within said nucleic acid.

2. A method as claimed in claim 1 wherein according to step (c), a signal is generated from said oligonucleotide probes which is proportional to the amount of living cell originating nucleic acid.

3. A method as claimed in claim 1 wherein the majority of nucleic acid detected originates from living cells.

4. A method as claimed in claim 3 wherein at least about 65% of the nucleic acid detected originates from living cells.

5. A method as claimed in claim 4 wherein at least 75% of the nucleic acid detected originated from living cells.

6. A method as claimed in claim 5 wherein at least about 85% of the nucleic acid detected originates from living cells.

7. A method as claimed in claim 1 wherein the viability probe modifies the nucleic acid by at least one of labelling the nucleic acid and inactivating the nucleic acid.

8. A method as claimed claim 1 wherein the viability probe selectivity modifies DNA.

9. A method as claimed in claim 1 wherein the detection method involves binding of an oligonucleotide probe to a target sequence within the nucleic acid molecule from living cells.

10. A method as claimed in claim 1 wherein the detection method involves amplification of a region of nucleic acid from the living cells in the sample.

11. A method of detecting cells in a sample, said method comprising:
   (a) contacting the sample with a viability probe which labels the nucleic acid of dead cells within the sample,
   wherein said viability probe selectively interacts with nucleic acid from dead cells, such that said nucleic acid in living cells remain unmodified by the viability probe;
   (b) lying the cells after step (a) and after cell lysis allowing the nucleic acid from both living and dead cells to mix prior to performance of step (c);
   (c) separating the nucleic acid from the cells into labeled and non-labeled fractions; and (d) detecting the nucleic acid in one or both of the fractions.

12. A method as claimed in claim 1 wherein the viability probe covalently binds to dead cell nucleic acid.

13. A method as claimed in claim 1 wherein the viability probe is a dye, a peptide, an oligonucleotide or a nucleic acid degrading enzyme, wherein said oligonucleotide comprises an inhibiting moiety, wherein said inhibiting moiety is EMA or 4'-AMDMIP.

14. A method as claimed in claim 13 wherein the viability probe is selected from ethidium bromide monoazide (EMA), 4'-AMDMIP, AMIP, 5-MIP (5-methylisopsoralen) and a DNase.

15. A method as claimed in claim 1 wherein the modification caused by the viability probe is non-reversible.

16. A method as claimed in claim 1 wherein the viability probe also modifies free nucleic acid present in the sample.

17. A method as claimed in claim 11 wherein the viability probe covalently binds to dead cell nucleic acid.

18. A method as claimed in claim 11 wherein the viability probe is a dye, a peptide, or an oligonucleotide, wherein said oligonucleotide comprises an inhibiting moiety, wherein said inhibiting moiety is EMA or 4'-AMDMIP.

19. A method as claimed in claim 18 wherein the viability probe is selected from ethidium bromide monoazide (EMA), 4'-AMDMIP, AMIP, and 5-MIP (5-methylisopsoralen).

20. A method as claimed in claim 11 wherein the viability probe also modifies free nucleic acid present in the sample.

* * * * *

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial sequence
<220> FEATURE:
<221> NAME/KEY: misc_feature
<222> LOCATION: ()..()
<223> OTHER INFORMATION: primer

<400> SEQUENCE: 1
tggctcagat tgaacgctgg cggc                                          24

<210> SEQ ID NO 2
<211> LENGTH: 20
<212> TYPE: DNA
<213> ORGANISM: artificial sequence
<220> FEATURE:
<221> NAME/KEY: misc_feature
<222> LOCATION: ()..()
<223> OTHER INFORMATION: primer

<400> SEQUENCE: 2
```

-continued

```
cttgttacga cttcacccca                                              20

<210> SEQ ID NO 3
<211> LENGTH: 25
<212> TYPE: DNA
<213> ORGANISM: artificial sequence
<220> FEATURE:
<221> NAME/KEY: misc_feature
<222> LOCATION: ()..()
<223> OTHER INFORMATION: primer

<400> SEQUENCE: 3
ctgaatttga taccttaagt gcagc                                        25

<210> SEQ ID NO 4
<211> LENGTH: 22
<212> TYPE: DNA
<213> ORGANISM: artificial sequence
<220> FEATURE:
<221> NAME/KEY: misc_feature
<222> LOCATION: ()..()
<223> OTHER INFORMATION: primer

<400> SEQUENCE: 4
aggcacgcct aaacctatag ct                                           22

<210> SEQ ID NO 5
<211> LENGTH: 35
<212> TYPE: DNA
<213> ORGANISM: artificial sequence
<220> FEATURE:
<221> NAME/KEY: misc_feature
<222> LOCATION: ()..()
<223> OTHER INFORMATION: probe

<400> SEQUENCE: 5
tctccttgct catctttagg ataaattctt tcaca                             35
```